(12) United States Patent
Cunningham et al.

(10) Patent No.: US 11,128,601 B2
(45) Date of Patent: Sep. 21, 2021

(54) METHODS, SYSTEMS, AND COMPUTER PROGRAM PRODUCTS FOR COMPILING INFORMATION FOR USE IN A COMMAND SCRIPT FOR A PRODUCT DISPENSING SYSTEM

(75) Inventors: Paul Joseph Cunningham, Hillsborough, NC (US); Jonathan Anthony Mitchall, Cary, NC (US); Andrew Keller McCarron, Raleigh, NC (US); Stefano Bresolin, Garner, NC (US); Vick Allen Hubbard, Wake Forest, NC (US)

(73) Assignee: SPENCER HEALTH SOLUTIONS, LLC, Durham, NC (US)

( * ) Notice: Subject to any disclaimer, the term of this patent is extended or adjusted under 35 U.S.C. 154(b) by 1581 days.

(21) Appl. No.: 12/199,602

(22) Filed: Aug. 27, 2008

(65) Prior Publication Data

US 2009/0103127 A1 Apr. 23, 2009

Related U.S. Application Data

(60) Provisional application No. 60/968,358, filed on Aug. 28, 2007.

(51) Int. Cl.
*G16H 20/13* (2018.01)
*G06F 8/41* (2018.01)
(Continued)

(52) U.S. Cl.
CPC ........ *H04L 63/0245* (2013.01); *G06F 3/1205* (2013.01); *G06F 3/1248* (2013.01);
(Continued)

(58) Field of Classification Search
CPC ..................................................... G06F 8/4435
(Continued)

(56) References Cited

U.S. PATENT DOCUMENTS

| 5,337,919 A | 8/1994 | Spaulding et al. |
| 5,468,110 A | 11/1995 | McDonald et al. |

(Continued)

FOREIGN PATENT DOCUMENTS

EP 1 739 520 A1 1/2007

OTHER PUBLICATIONS

Merriam-Webster Dictionary, May 30, 2012, http://www.merriam-webster.com/dictionary/extract.*

(Continued)

*Primary Examiner* — Peter K Huntsinger
(74) *Attorney, Agent, or Firm* — Myers Bigel, P.A (57) ABSTRACT

Information for use in a command script for a product dispensing system is compiled by sniffing packets associated with a print job that contains information associated with a product to be dispensed, filtering the packets so as to remove fields not associated with the print job, and combining the filtered packets to generate contiguous data associated with the print job. A command script for a product dispensing system is generated by receiving data associated with a print job that contains information associated with a product to be dispensed, extracting the information associated with the product from the print job data, organizing the information associated with the product into discrete informational units, and generating the command script based on the organized discrete information units.

28 Claims, 6 Drawing Sheets

(51) Int. Cl.
  *H04L 29/06* (2006.01)
  *G06F 3/12* (2006.01)
(52) U.S. Cl.
  CPC .......... *G06F 3/1285* (2013.01); *G06F 8/4435*
      (2013.01); *G16H 20/13* (2018.01)
(58) Field of Classification Search
  USPC .......................................... 235/375; 358/1.15
  See application file for complete search history.

(56) References Cited

U.S. PATENT DOCUMENTS

| | | | |
|---|---|---|---|
| 5,914,955 A * | 6/1999 | Rostoker et al. | .......... 370/395.5 |
| 6,240,394 B1 | 5/2001 | Uecker et al. | |
| 6,735,497 B2 | 5/2004 | Wallace et al. | |
| 6,772,943 B2 * | 8/2004 | Segal | ............................ 235/375 |
| 7,096,212 B2 | 8/2006 | Tribble et al. | |
| 7,225,052 B2 | 5/2007 | Foote et al. | |
| 7,379,203 B2 | 5/2008 | Kofman et al. | |
| 2002/0080393 A1 | 6/2002 | Leonard | |
| 2003/0050731 A1* | 3/2003 | Rosenblum | ......... G06F 19/3462 700/232 |
| 2003/0179400 A1* | 9/2003 | Kofman et al. | ............. 358/1.13 |
| 2003/0188012 A1* | 10/2003 | Ford | ....................... G06F 21/31 709/238 |
| 2004/0107022 A1 | 6/2004 | Gomez | |
| 2007/0164096 A1 | 7/2007 | Banfield et al. | |

OTHER PUBLICATIONS

Merriam-Webster Dictionary, May 31, 2012, http://www.merriam-webster.com/dictionary/remove.*
International Search Report and Written Opinion (12 pages) corresponding to International Application No. PCT/US2008/010180; dated Dec. 16, 2008.
Canadian Office Action Corresponding to Canadian Patent Application No. 2,695,539; dated Nov. 1, 2013; 4 Pages.
Canadian Office Action Corresponding to Canadian Patent Application No. 2,695,539; dated Nov. 28, 2014; 7 Pages.

* cited by examiner

METHODS, SYSTEMS, AND COMPUTER PROGRAM PRODUCTS FOR COMPILING INFORMATION FOR USE IN A COMMAND SCRIPT FOR A PRODUCT DISPENSING SYSTEM

CROSS-REFERENCE TO RELATED APPLICATION

This application claims the benefit of and priority to U.S. Provisional Patent Application No. 60/968,358, filed Aug. 28, 2007, the disclosure of which is hereby incorporated herein by reference as if set forth in its entirety.

BACKGROUND OF THE INVENTION

The present invention relates to methods, systems, and computer program products for operating product dispensing systems and, more particularly, to methods, systems, and computer program products for sending commands to product dispensing systems.

Pharmacy automation devices, such as automated prescription filling systems and work flow systems, may require information from an external system, such as a pharmacy host system, to properly dispense a medication. Because the pharmacy host systems may use various types of software applications, the automated prescription filling system may use an interface that is incompatible with the communication protocol and/or the command library used by the pharmacy host system.

Many conventional pharmacy host systems print medication labels for placement on a vial and/or print a paper copy that includes a description of a medication for a patient when filling a prescription. Conventional systems have intercepted the output from a printer port of the pharmacy host system and used the captured information to generate a command for an automated prescription filling system. While this may work when a printer is connected to the serial or parallel port of the pharmacy host system, many pharmacies locate their printers on a network, such as an Ethernet network.

SUMMARY OF THE INVENTION

According to some embodiments of the present invention, a method of compiling information for use in a command script for a product dispensing system includes sniffing packets associated with a print job that contains information associated with a product to be dispensed, filtering the packets so as to remove fields not associated with the print job, and combining the filtered packets to generate contiguous data associated with the print job.

In other embodiments, the method further includes extracting the information associated with the product from the contiguous data and organizing the information associated with the product into discrete informational units.

In still other embodiments, the discrete information units include discrete textual items.

In still other embodiments, each of the discrete textual items includes an acronym, word, number, and/or phrase.

In still other embodiments, organizing the information associated with the product includes associating Cartesian coordinates with each of the discrete textual items, associating an orientation indicator for each of the discrete textual items, and/or associating a page number of the print job for each of the discrete textual items that identifies a page that the respective textual item would have printed on.

In still other embodiments, the packets comprise Page Description Language (PDL) data.

In still other embodiments, extracting the information includes extracting Postscript or Printer Command Language (PCL) data.

In still other embodiments, extracting the information includes extracting raster graphics or binary data and performing optical character recognition on the raster graphics or binary data.

In still other embodiments, the packets are TCP/IP packets.

In still other embodiments, sniffing the packets includes sniffing the packets via a network hub that is configured to present all packet traffic to all ports on the hub.

In still other embodiments, sniffing the packets comprises sniffing the packets via a switch that is configured to mirror traffic destined for at least one printer to a port on the switch.

In still other embodiments, the product dispensing system is a pharmaceutical product dispensing system.

In still other embodiments, the product dispensing system is a tablet dispensing system.

In further embodiments of the present invention, a method for generating a command script for a product dispensing system includes receiving data associated with a print job that contains information associated with a product to be dispensed, extracting the information associated with the product from the print job data, organizing the information associated with the product into discrete informational units, and generating the command script based on the organized discrete information units.

In still further embodiments of the present invention, the discrete information units comprise discrete textual items.

In still further embodiments, each of the discrete textual items includes an acronym, word, number, and/or phrase.

In still further embodiments, organizing the information associated with the product includes associating Cartesian coordinates with each of the discrete textual items, associating an orientation indicator for each of the discrete textual items, and/or associating a page number of the print job for each of the discrete textual items that identifies a page that the respective textual item would have printed on.

In still further embodiments, the method further comprises generating a bitmap file containing the extracted information associated with the product.

In still further embodiments, the method further includes identifying script fields in the bitmap file, determining Cartesian coordinates for each of the identified script fields, determining an orientation indicator for each of the identified script fields, and/or determining a page number of the print job for each of the identified script fields that identifies a page that the respective script field would have printed on.

In still further embodiments, the method further includes associating respective ones of the script fields with respective ones of the discrete textual items such that each of the script fields is associated with at least one of the discrete textual items. Generating the command script includes generating the command script based on the associations between the script fields and the discrete textual items.

In still further embodiments, extracting the information includes extracting Postscript or Printer Command Language (PCL) data.

In still further embodiments, extracting the information includes extracting raster graphics or binary data and performing optical character recognition on the raster graphics or binary data.

In still further embodiments, the product dispensing system is a pharmaceutical product dispensing system.

In still further embodiments, the product dispensing system is a tablet dispensing system.

Although described above primarily with respect to method aspects of the present invention, it will be understood that the present invention may be embodied as methods, systems, and/or computer program products.

DETAILED DESCRIPTION OF EXEMPLARY EMBODIMENTS

Specific exemplary embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the particular exemplary embodiments illustrated in the accompanying drawings is not intended to be limiting of the invention. In the drawings, like numbers refer to like elements.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention may be embodied as methods, systems, and/or computer program products. Accordingly, the present invention may be embodied in hardware and/or in software (including firmware, resident software, microcode, etc.). Furthermore, the present invention may take the form of a computer program product comprising a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Some embodiments of the present invention may provide for the capture and processing of print job information associated with a product to be dispensed that is sent from, for example, a pharmacy host system to a printer. The print job information can be captured by monitoring packet flow from a network access port, such as a hub or switch. According to some embodiments of the present invention, the packets comprising the print job can be filtered to remove fields not associated with the print job and the remaining fields combined to generate a contiguous block of data that is associated with the print job. The contiguous block of data may then be processed to extract the information associated with the product to be dispensed. The information associated with the product to be dispensed is then organized into discrete informational units, such as discrete textual items. In some embodiments, the placement of the discrete textual items on a label or page is identified through the use of Cartesian coordinates, an orientation indicator, and/or a page number of the page or label on which the textual item would have printed. The print information may also be displayed via a bitmap file, for example, allowing the identification of various script fields and their placement on the label/page using Cartesian coordinates, an orientation indicator, and/or a page number of the page or label on which the script field would have printed. The identified script fields can then be associated with the textual items extracted from the print job information based on matches between the Cartesian coordinates, orientation indicator, and/or page number between the script fields and the textual items. A command script used to operate a product dispensing system, such as a pharmaceutical tablet dispensing robot, can then be generated based on the associations between the script fields and the textual items extracted from the print job information.

For purposes of illustration, embodiments of the present invention are described herein in the context of a pharmacy application in which prescriptions for customers are filled through an automated product dispensing system. It will be understood that the present invention is not limited to pharmacy applications or any particular type of product dispensing system, but is applicable generally to any type of automated product dispensing system capable of carrying out the operations described herein.

Figure 1:
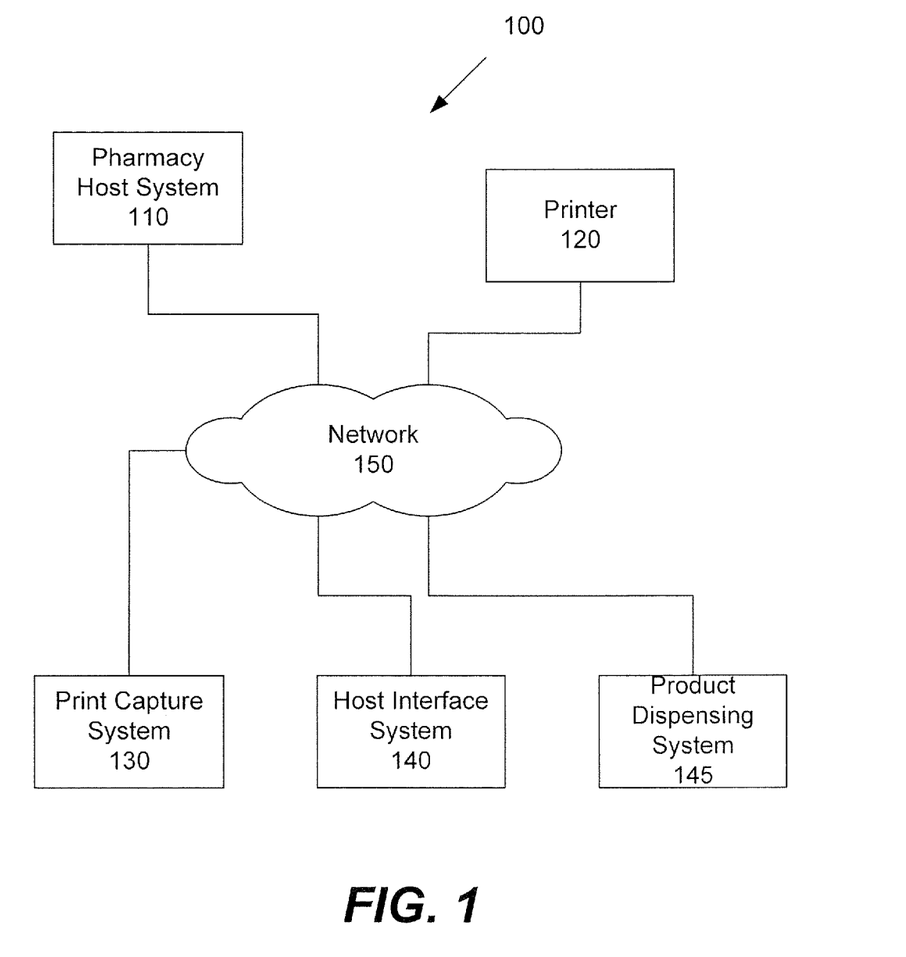
FIG. 1 is a block diagram of a communication network for capturing information for use in a command script for a product dispensing system in accordance with some embodiments of the present invention.

Referring to FIG. 1, a communication network 100, in accordance with some embodiments of the present invention, comprises a pharmacy host system 110, one or more printers 120, a print capture system 130, a host interface system 140, and a product dispensing system 145 that are coupled via network 150 as shown. The network 150 may be a global network, such as the Internet or other publicly accessible network. Various elements of the network may be interconnected by a wide area network, a local area network, an Intranet, and/or other private network, which may not be accessible by the general public. Thus, the network 150 may represent a combination of public and private networks or a virtual private network (VPN).

The pharmacy host system 110 may be configured to manage and fill prescriptions for customers. Labels for vials and/or paperwork associated with a prescription may be printed on one or more printers 120. The print capture system 130 may be configured to monitor packet traffic on the network 150 through use of packet sniffing functionality so as to capture packets associated with a print job that contains information associated with a product to be dispensed in filling a prescription. The packets comprising the print job can be filtered to remove fields not associated with the print job and the remaining fields combined to generate a contiguous block of data that is associated with the print job.

The host interface system 140 includes a host interface application that is configured to receive commands from the pharmacy host system 110 intended for the product dispensing system 145 and to perform any necessary conversion and/or formatting before communicating the command to the product dispensing system 145. The host interface system 140 application software may be extended by developing and adding new host and automation interfaces. A command to the product dispensing system 145 may comprise a script that includes one or more fields. In the context of a pharmacy application, a command script may comprise all of the available patient and drug information required to describe a single prescription for a patient.

According to some embodiments of the present invention, the host interface system 140 may be configured to receive the contiguous block of data that is associated with the print job and to extract the information associated with the product to be dispensed. The information associated with the product to be dispensed may then be organized into discrete informational units, such as discrete textual items. In some embodiments, the placement of the discrete textual items on a label or page is identified through the use of Cartesian coordinates, an orientation indicator, and/or a page number of the page or label on which the textual item would have printed.

The host interface system 140 may be further configured to provide for display of the print information via a bitmap file. This may allow a user, for example, to identify the various locations on the label/page of script fields that are used in generating a command script for the product dispensing system. The placement of the script fields may be identified using Cartesian coordinates, an orientation indicator, and/or a page number of the page or label on which the script field would have printed. The identified script fields can then be associated with the textual items extracted from the print job information based on matches between the Cartesian coordinates, orientation indicator, and/or page number between the script fields and the textual items. The host interface system 140 may then generate a command script to instruct, for example, the product dispensing system 145 to fill a prescription based on the associations between the script fields and the textual items extracted from the print job information. The product dispensing system 145 may be a robotic or semi-automatic dispensing system that dispenses medications, such as pills, tablets, and the like. It will be understood, however, that the present invention is not limited to any particular type of dispensing system or product to be dispensed.

It is not uncommon for the pharmacy host system 110 to change or upgrade software applications, which can result in changes in the way that commands for the product dispensing system 145 are communicated/formatted. Such changes in the host system 110 software have traditionally resulted in corresponding changes to the host interface system 140 software. Advantageously, embodiments of the present invention may reduce or eliminate the need for any such changes to the host interface system 140 software as the information used to generate the commands to the product dispensing system 145 is obtained from the print job sent to the printer 120 rather than from the command communicated from the pharmacy host system 110.

Although FIG. 1 illustrates an exemplary communication network, it will be understood that the present invention is not limited to such configurations, but is intended to encompass any configuration capable of carrying out the operations described herein. Moreover, functionality described as associated with the pharmacy host system 110, the print capture system 130, the host interface system 140, and/or the product dispensing system 145 is merely exemplary and various functionality may be moved between different ones of the aforementioned systems in accordance with other embodiments of the present invention.

Figure 2:
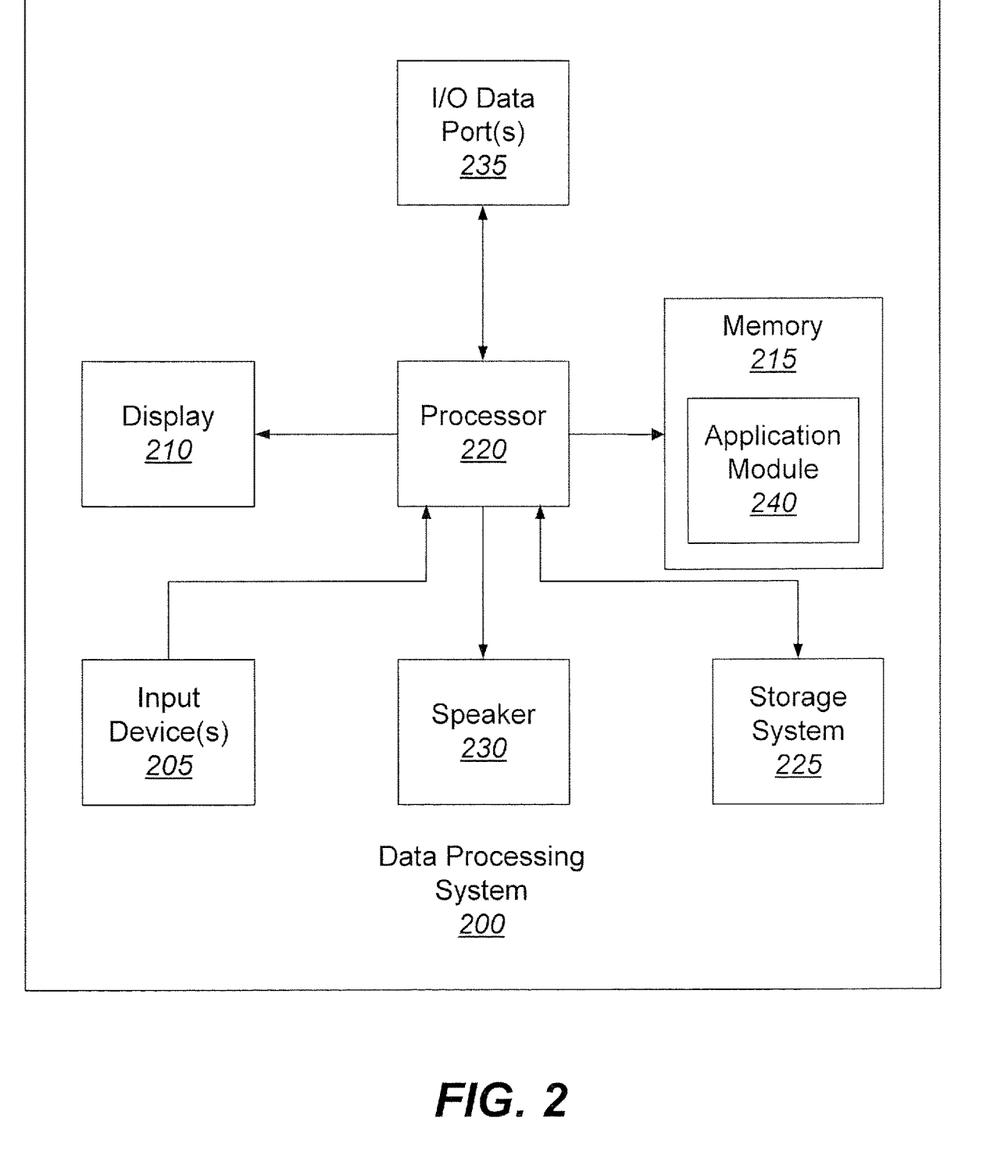
FIG. 2 is a block diagram that illustrates a data processing system in accordance with some embodiments of the present invention.

FIG. 2 illustrates a data processing system 200 that may be used, for example, to implement the pharmacy host system 110, print capture system 130, and/or host interface system 140 in accordance with some embodiments of the present invention. The data processing system 200 comprises input device(s) 205, such as a keyboard or keypad, a display 210, and a memory 215 that communicate with a processor 220. The data processing system 200 may further comprise a storage system 225, a speaker 230, and an I/O data port(s) 235 that also communicate with the processor 220. The storage system 225 may include removable and/or fixed media, such as floppy disks, ZIP drives, hard disks, or the like as well as virtual storage such as a RAMDISK. The I/O data port(s) 235 may be used to transfer information between the data processing system 200 and another computer system or a network (e.g., the Internet). These components may be conventional components, such as those used in many conventional computing devices, and their functionality, with respect to conventional operations, is generally known to those skilled in the art. The memory 215 may be configured with an application module 240 that may be used to provide the functionality associated with the pharmacy host system 110, print capture system 130, and/or host interface system 140 in accordance with some embodiments of the present invention.

Figure 3:
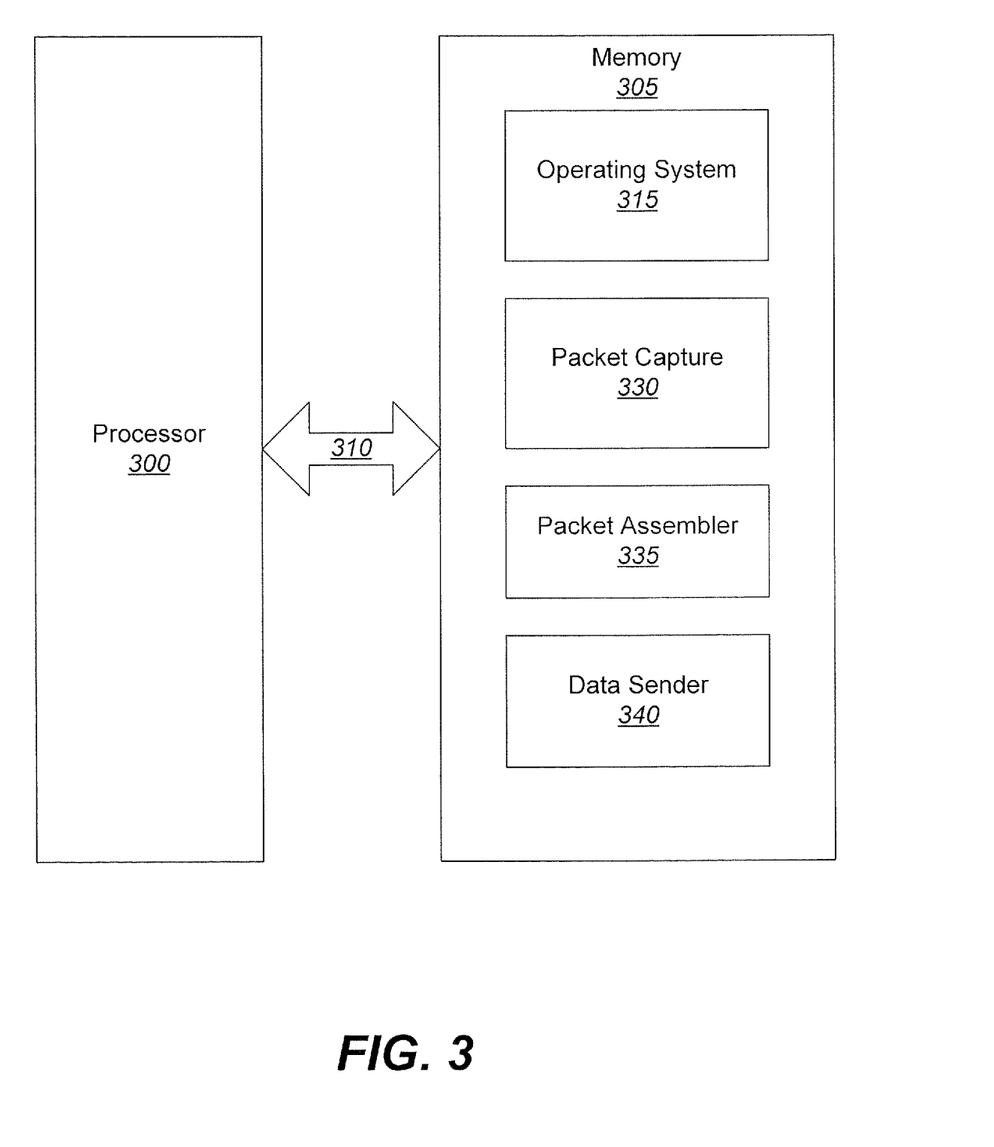
FIG. 3 is a block diagram that illustrates a software/hardware architecture for a print capture system in accordance with some embodiments of the present invention.

FIG. 3 illustrates a processor 300 and memory 305 that may be used in embodiments of data processing systems, such as the print capture system 130 of FIG. 1 and the data processing system 200 of FIG. 2 in accordance with some embodiments of the present invention. The processor 300 communicates with the memory 305 via an address/data bus 310. The processor 300 may be, for example, a commercially available or custom microprocessor. The memory 305 is representative of the one or more memory devices containing the software and data used to capture packets associated with a print job and transmitted over a network in accordance with some embodiments of the present invention. The memory 305 may include, but is not limited to, the following types of devices: cache, ROM, PROM, EPROM, EEPROM, flash, SRAM, and DRAM.

As shown in FIG. 3, the memory 305 may contain up to four or more categories of software and/or data: an operating system 315, a packet capture module 330, a packet assembler module 335, and a data sender module 340. The operating system 315 generally controls the operation of the data processing system. In particular, the operating system 315 may manage the data processing system's software and/or hardware resources and may coordinate execution of programs by the processor 300. The packet capture module 330 may provide packet sniffing functionality by using the open source WINPCAP™ library to capture Ethernet packets sent to one or more printers. WINPCAP™ is an open source software driver designed for link-layer network access in WINDOWS™ environments. It allows the print capture system 130 to capture network packets that contain label data for a prescription.

In accordance with various embodiments of the present invention, two possible hardware configurations may be used to implement packet capturing. Both methods provide Ethernet capture ability without exposing all Ethernet traffic to the sniffer. Only label information will be processed by the print capture system 130 keeping other sensitive information secure.

Figure 4:
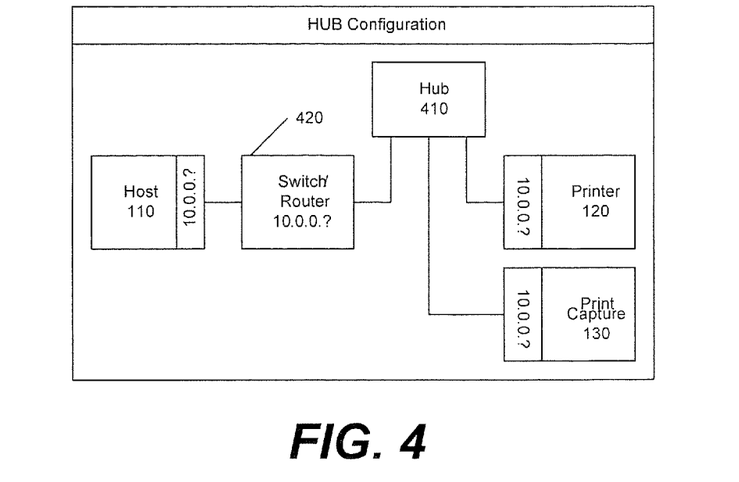
FIG. 4 is a block diagram of the print capture system connected to a network in a hub configuration in accordance with some embodiments of the present invention.

The first configuration is illustrated in FIG. 4 in which an Ethernet hub 410 is placed in the network that the target printer is connected to. The print capture system 130 is then plugged into the same hub 410. This configuration uses a hub that presents all Ethernet traffic on all ports. The host system 110 may be connected to the hub 410 via a switch/router 420.

Figure 5:
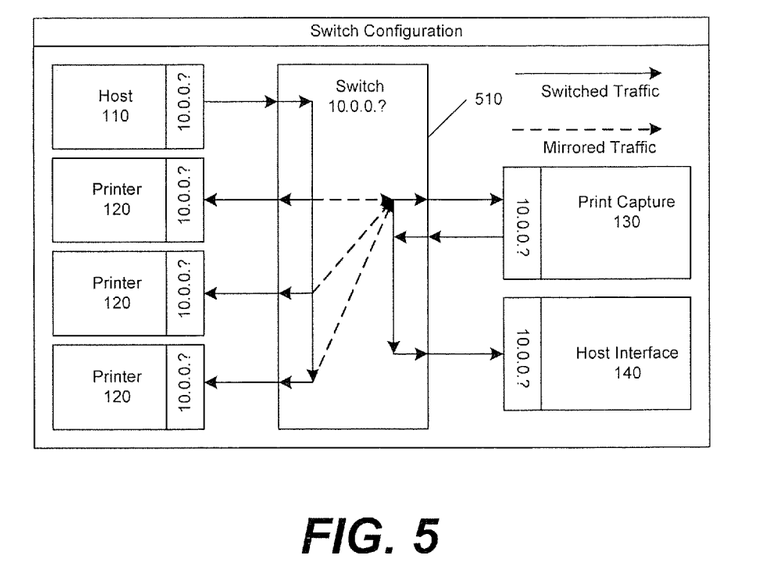
FIG. 5 is a block diagram of the print capture system connected to a network in a switch configuration in accordance with some embodiments of the present invention.

The second configuration is illustrated in FIG. 5 in which a managed Ethernet switch 510 is used. Printer ports on the switch 510 have their traffic mirrored to a port that is connected to the print capture system 130. Only packets sent to and from mirrored printer ports are sent to the print capture system. In this configuration a second Ethernet adapter may be used to send the reconstructed label data, i.e., the contiguous block of data that is extracted from the packets by filtering fields not associated with the print job to the host interface system 140.

Returning to FIG. 3, the packet assembler module 335 may be configured to filter the captured packets using a WINDOWS™ service, for example. Ethernet, IP, and/or TCP headers are examined and removed to generate a contiguous block of data that is associated with the print job. In the context of a pharmacy application in which labels are printed for vials when filling a prescription, the contiguous block of data may be referred to as reconstructed label data.

The data sender module 340 may be configured to send the contiguous block of data associated with the print job that is generated by the packet assembler module 335 to the host interface system 140.

Although FIG. 3 illustrates exemplary hardware/software architectures that may be used in data processing systems, such as the print capture system 130 of FIG. 1 and/or the data processing system 200 of FIG. 2, for capturing packets from a network that are associated with a print job, it will be understood that the present invention is not limited to such a configuration but is intended to encompass any configuration capable of carrying out operations described herein. Moreover, the functionality of the print capture system 130 of FIG. 1, the data processing system 200 of FIG. 2, and/or the hardware/software architecture of FIG. 3 may be implemented as a single processor system, a multi-processor system, or even a network of stand-alone computer systems, in accordance with various embodiments of the present invention.

Computer program code for carrying out operations of data processing systems discussed above with respect to FIG. 3 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Figure 6:
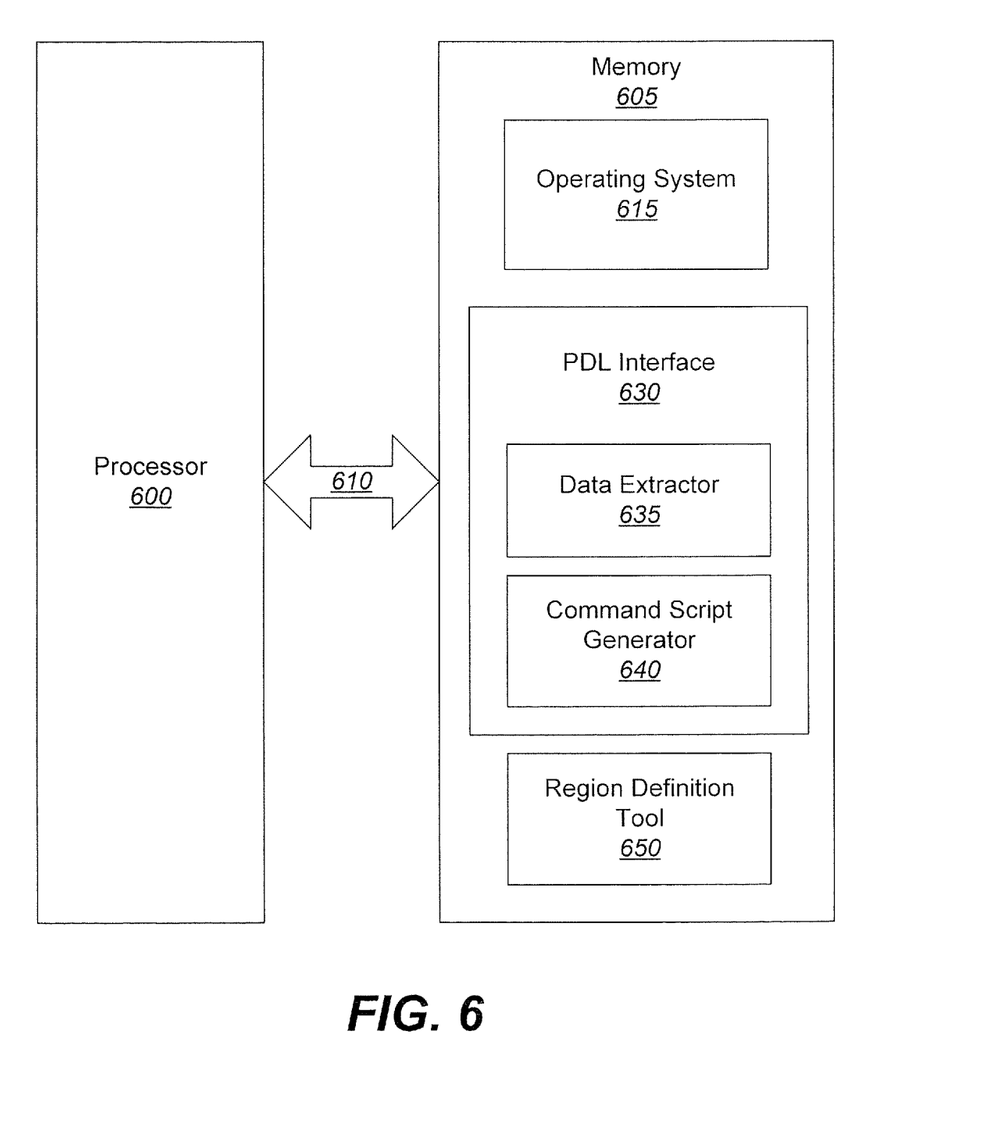
FIG. 6 is a block diagram that illustrates a software/hardware architecture for a host interface system in accordance with some embodiments of the present invention.

FIG. 6 illustrates a processor 600 and memory 605 that may be used in embodiments of data processing systems, such as the host interface system 140 of FIG. 1 and the data processing system 200 of FIG. 2 in accordance with some embodiments of the present invention. The processor 600 communicates with the memory 605 via an address/data bus 610. The processor 600 may be, for example, a commercially available or custom microprocessor. The memory 605 is representative of the one or more memory devices containing the software and data used to generate a command script for a product dispensing system in accordance with some embodiments of the present invention. The memory 605 may include, but is not limited to, the following types of devices: cache, ROM, PROM, EPROM, EEPROM, flash, SRAM, and DRAM.

As shown in FIG. 6, the memory 605 may contain up to two or more categories of software and/or data: an operating system 615, a Page Description Language (PDL) interface module 630, and a region definition tool 650. The PDL interface module 630 includes a data extractor module 635 and a command script generator 640. The operating system 615 generally controls the operation of the data processing system. In particular, the operating system 615 may manage the data processing system's software and/or hardware resources and may coordinate execution of programs by the processor 600.

The PDL interface module 630 may be configured to receive the contiguous data associated with the print job, which may be referred to as the reconstructed label data, from the print capture system 130. Using the data extractor module 635, regions file generated by the region definition tool 650, and command script generator 640, the PDL interface module 630 may generate a command script that can be communicated to the product dispensing system 145 to dispense a product.

The data extractor module 635 may be configured to extract the information associated with the product from the contiguous data associated with the print job. In accordance with various embodiments of the present invention, the contiguous data may be Printer Command Language (PCL) data, Postscript data, raster graphics data, or binary data. If the contiguous data is raster graphics data or binary data, optical character recognition processing may be performed to extract the product information therefrom. The contiguous data associated with the print job is described herein as being captured from the network using the print capture system 130. In other embodiments of the present invention, the data containing information associated with the product to be dispensed may be provided to the host interface system 140 via a file, via a communication protocol, or other means of input.

Figure 7:
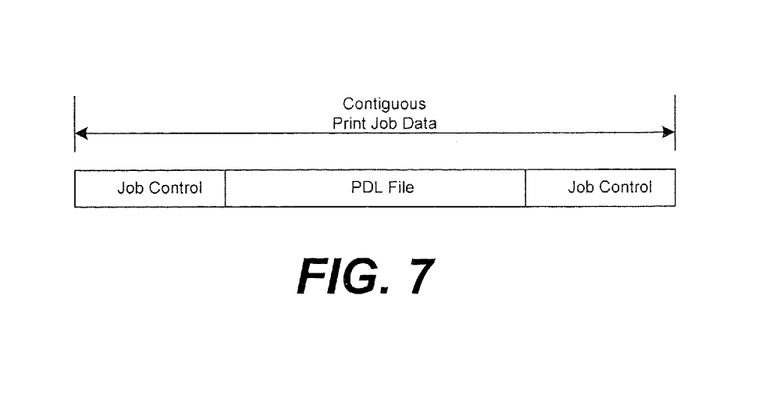
FIG. 7 is a block diagram that illustrates captured print job data in accordance with some embodiments of the present invention.

The data extractor module 635 may extract the information associated with the product to be dispensed by filtering the job control fields from the contiguous print job data so as to obtain the PDL file as shown in FIG. 7. The job control fields may be character strings that identify the beginning and end of the print data. These characters are specific to the language used to define printer commands to the printer.

Once the information associated with the product to be dispensed is extracted from the print job, it may be organized into discrete information units, such as discrete textual items. The discrete textual items may include acronyms, words, numbers, and/or phrases in accordance with various embodiments of the present invention. The data extractor module may construct a text item table for all of the text blocks contained in the print job. Each row of the text item table may comprise an information unit, such as a text item, along with specific attributes. In accordance with some embodiments of the present invention, the attributes are the starting location of the text, the orientation of the text, and the document page number of the text. The starting location is comprised of an X and a Y Cartesian coordinate pair. The coordinate unit of measure is a decipoint equivalent to $1/720^{th}$ of an inch.

The data extractor module 635 may be further configured to generate a bitmap file that contains the extracted information associated with the product to be dispensed. The region definition tool 650 may identify script fields contained in the bitmap file output from the data extractor module 635 and their placement on the label/page using Cartesian coordinates, an orientation indicator, and/or a page number of the page or label on which the script field would have printed. For a pharmacy application in which medicines are dispensed to fill prescriptions, the script fields may include, but are not limited to, the example fields set forth below:

| | | |
|---|---|---|
| RXORDERNUMBER | PATIENTFIRSTNAME | PATIENTMIDDLEINITIAL |
| PATIENTLASTNAME | PATIENTADDRESS | PATIENTCITYSTATEZIP |
| DRUGNDC | DISPENSEDDRUGNAME | PRESCRIBEDDRUGNAME |
| QUANTITY | DRUGMFG | DOCTORNAME |
| DOCTORDEA | RPHFIELD | TECHNICIAN |
| SIGFIELD | BARCODE | REFILLNUMBER |
| TOTALREFILLS | REFILLDATE | FILLDATE |
| ORIGDATE | STOPDATE | EXPIREDATE |
| DAYSSUPPLY | DRUGCLASS | PATIENTSSN |
| WARNING1 | WARNING2 | WARNING3 |
| WARNING4 | PCKEY | SOURCETERMINAL |
| URGENCY | VIALSIZE | ACTION |
| STORENUM | STOREADDRESS | STORECITYSTATEZIP |
| STOREPHONENUM | GENERICFIELD1 | GENERICFIELD2 |
| GENERICFIELD3 | GRAPHICSFILEPATH | SCRIPTTIMESTAMP |
| USEALTINVENTORY | FREEFORMREFILL | NONSAFETYCAP |
| REFILLSLEFT | PHARMACISTNAME | DRUGDESCRIPTION |
| UNICODESIGFIELD | | |

The particular script fields and their placement on the label/page may be output to a regions file. The location and size of a given region for a particular script field may be specified via a human interface. In some embodiments of the present invention, the region definition tool 650 may use a bitmap representation of a sample label that has been produced by the data extractor module 635. The bitmap is displayed to provide the user a means of seeing a given region superimposed on it. This may allow the user to more rapidly determine the location and size of the regions being defined.

The identified script fields in the regions file can then be associated with the textual items extracted from the print job information based on matches between the Cartesian coordinates, orientation indicator, and/or page number between the script fields and the textual items. A command script used to operate the product dispensing system 145, such as a pharmaceutical tablet dispensing robot, can then be generated based on the associations between the script fields and the textual items extracted from the print job information.

Although FIG. 6 illustrates exemplary hardware/software architectures that may be used in data processing systems, such as the host interface system 140 of FIG. 1 and/or the data processing system 200 of FIG. 2, for receiving data from an external system and translating that data into a uniform set of one or more commands and data recognizable to another system, it will be understood that the present invention is not limited to such a configuration but is intended to encompass any configuration capable of carrying out operations described herein. Moreover, the functionality of the host interface system 130 of FIG. 1, the data processing system 200 of FIG. 2, and/or the hardware/software architecture of FIG. 6 may be implemented as a single processor system, a multi-processor system, or even a network of stand-alone computer systems, in accordance with various embodiments of the present invention.

Computer program code for carrying out operations of data processing systems discussed above with respect to FIG. 6 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Figure 8:
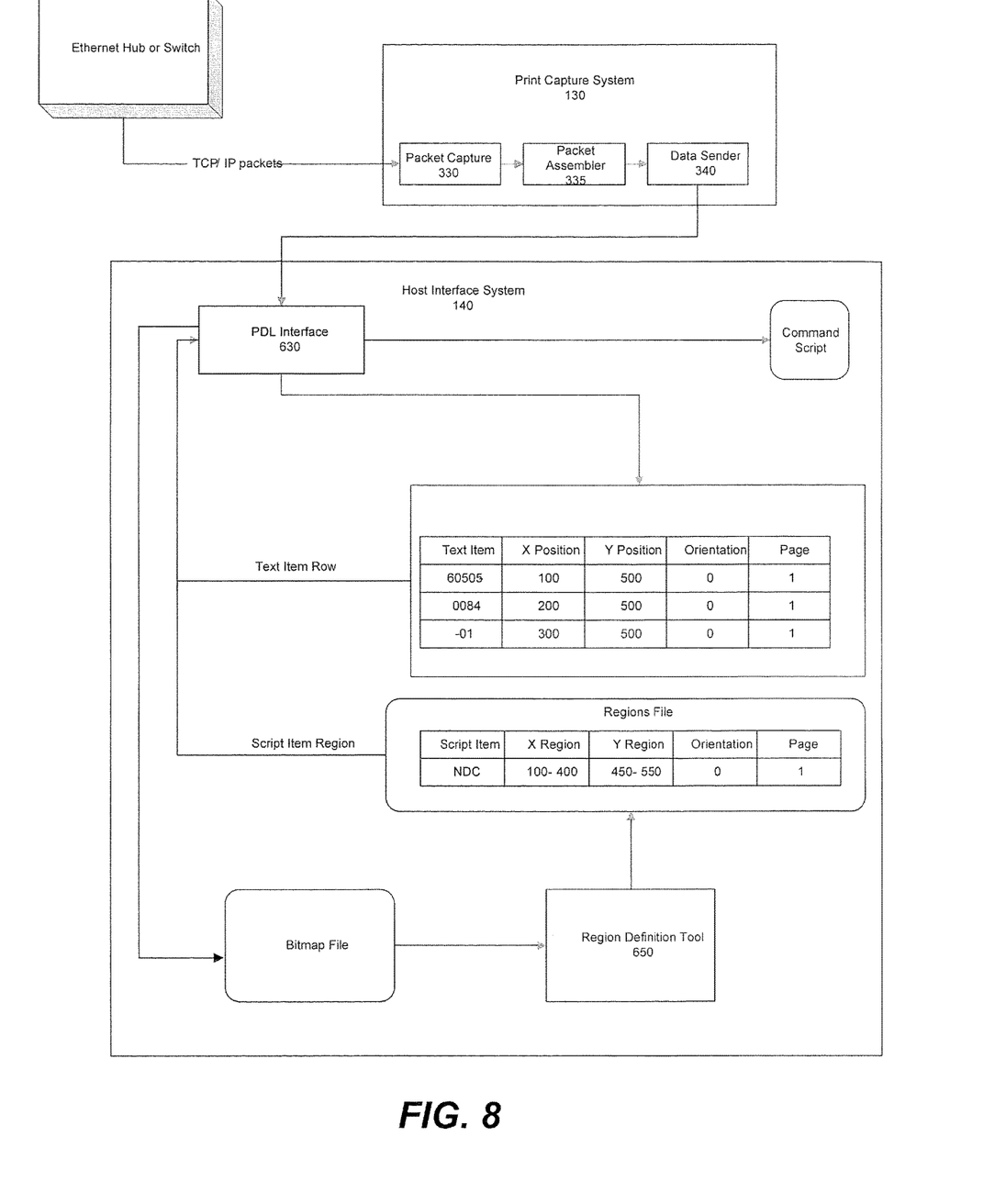
FIG. 8 is a data flow diagram that illustrates operations of methods, systems, and computer program products for sending commands to product dispensing systems in accordance with some embodiments of the present invention.

FIG. 8 is a data flow diagram that illustrates operations of methods, systems, and computer program products for sending commands to product dispensing systems in accordance with some embodiments of the present invention. As shown in FIG. 8, the print capture system 130 can sniff packets that are associated with a print job that contains information associated with a product to be dispensed from a network hub or switch using the packet capture module 330. The captured packets may then be filtered using the packet assembler module 335 to remove fields not associated with the print job. The filtered packets are combined to generate contiguous data associated with the print job, which may be called reconstructed label data in the context of a pharmacy application where the print job data corresponds to prescription information for a medication vial. The data sender module 340 communicates the data associated with the print job to the host interface system 140, which has a host interface application running thereon.

The host interface system 140 includes a PDL interface module 630 that extracts the information associated with the product to be dispensed from the contiguous data associated with the print job and organizes the extracted information into discrete information units, such as discrete textual items. As shown in the example of FIG. 8, the extracted information is organized into a text item table that associates Cartesian coordinates, an orientation indicator, and a page number of the print job on which the item would be printed for each of the text items. The example of FIG. 8 shows three text items with the aforementioned attributes as shown below:

| Text Item | X Position | Y Position | Orientation | Page |
|---|---|---|---|---|
| 60505- | 100 | 500 | 0 | 1 |
| 0084 | 200 | 500 | 0 | 1 |
| -01 | 300 | 500 | 0 | 1 |

The data extractor module 635 also generates a bitmap file from the contiguous print data associated with the product to be dispensed that can be processed by a region definition tool 650 to identify script fields therein. As shown below, a user may identify a script field, such as the script field NDC, and associate Cartesian coordinate regions, an orientation indicator, and a page number of the print job on which the script field would be printed with the script field.

The following information is written to the regions file for the script item NDC:

| Script Item | X Region | Y Region | Orientation | Page |
|---|---|---|---|---|
| NDC | 100-400 | 450-550 | 0 | 1 |

The command script generator 640 of the PDL interface 630 may then use the regions file and the text item table to generate a command script for operating the product dispensing system 145. Starting with a regions file produced by the region definition tool 650 and a command script whose fields are empty, the command script generator 640 inspects each row of the text item table. Each text item whose starting coordinates fall within a script field's region as specified in the regions file will be appended to a script field associated with the region containing the text item. When all rows of the text item table have been inspected in this manner the command script will contain the script items and associated informational units, e.g., textual items. In the example shown in FIG. 8, the text item NDC would be added to the command script along with its associated text of 60505-0084-01.

In the drawings and specification, there have been disclosed exemplary embodiments of the invention. Although specific terms are used, they are used in a generic and descriptive sense only and not for purposes of limitation, the scope of the invention being defined by the following claims.

That which is claimed:

1. A method, comprising:
performing operations on, a processor comprising:
sniffing traffic on a communication network to copy packets comprising a print job that contains product labeling information corresponding to a tangible product without facilitating communication of the packets comprising the p tnt job to a destination identified in the packets:
filtering the packets so as to remove fields from the packets that have been sniffed to generate filtered packets, the filtered packets comprising fields not removed from the packets that have been sniffed;
combining the filtered packets to generate contiguous data;
generating a command script based on the contiguous data;
sending the command script to a product dispensing system over the communication network; and
dispensing the tangible product using the product dispensing system responsive to receipt of the command script at, the product dispensing system.

2. The method of claim 1, further comprising:
extracting the product labeling information corresponding to the tangible product from the contiguous data; and
organizing the product labeling information corresponding to the tangible product into discrete informational units.

3. The method of claim 2, wherein the discrete information units comprise discrete textual items.

4. The method of claim 3, wherein each of the discrete textual items comprises an acronym, word, number, and/or phrase.

5. The method of claim 3, wherein organizing the information associated with the tangible product comprises:
associating Cartesian coordinates with each of the discrete textual items;
associating an orientation indicator for each of the discrete textual items; and/or associating a page number of the print job for each of the discrete textual items.

6. The method of claim 2, wherein the packets comprise Page Description Language (PDL) data.

7. The method of claim 6, wherein extracting the product labeling information comprises:
   extracting Postscript or Printer Command Language (PCL) data.

8. The method of claim 6, wherein extracting the product labeling information comprises:
   extracting raster graphics or binary data; and
   performing optical character recognition on the raster graphics or binary data.

9. The method of claim 1, wherein the packets are TCP/IP packets.

10. The method of claim 1, wherein sniffing the traffic comprises sniffing the packets via a network hub that is configured to present all packet traffic to all ports on the network hub.

11. The method of claim 1, wherein sniffing the traffic comprises sniffing the packets via a switch that is configured to mirror traffic destined for at least one printer to a port on the switch.

12. The method of claim 1, wherein the product dispensing system is a pharmaceutical product dispensing system and the tangible product comprises a tangible pharmaceutical product.

13. The method of claim 1, wherein the product dispensing system is a tablet dispensing system and the tangible product comprises a tablet.

14. A method, comprising:
   performing operations on a processor comprising:
   sniffing traffic on a communication network to copy packets comprising a print job that contains product labeling information corresponding to a tangible product without facilitating communication of the packets comprising the print job to a destination identified in the packets;
   extracting information corresponding to the tangible product from the packets comprising the print job;
   organizing the information corresponding to the tangible product that was extracted into discrete informational units;
   generating a command script based on the organized discrete informational units;
   sending the command script to a product dispensing system over the communication network: and
   dispensing the tangible product using the product dispensing system responsive to receipt of the command script at the product dispensing system.

15. The method of claim 14, wherein the discrete informational units comprise discrete textual items.

16. The method of claim 15, wherein each of the discrete textual items comprises an acronym, word, number, and/or phrase.

17. The method of claim 15, wherein organizing the information associated with the tangible product comprises:
   associating Cartesian coordinates with each of the discrete textual items;
   associating an orientation indicator for each of the discrete textual items; and/or
   associating a page number of the print job for each of the discrete textual items.

18. The method of claim 15, further comprising;
   generating a bitmap file containing the extracted information associated with the tangible product.

19. The method of claim 18, further comprising:
   identifying script fields in the bitmap file;
   determining Cartesian coordinate regions for each of the identified script fields;
   determining an orientation indicator for each of the identified script fields; and/or
   determining a page number of the print job for each of the identified script fields.

20. The method of claim 19, further comprising:
   associating respective ones of the script fields with respective ones of the discrete textual items such that each of the script fields is associated with at least one of the discrete textual items; and
   wherein generating the command script comprises generating the command script based on the associations between the script fields and the discrete textual items.

21. The method of claim 14 wherein extracting the information comprises:
   extracting Postscript or Printer Command Language (PCL) data.

22. The method of claim 14, wherein extracting the information comprises:
   extracting raster graphics or binary data; and
   performing optical character recognition on the raster graphics or binary data.

23. The method of claim 14, wherein the product dispensing system is a pharmaceutical product dispensing system and the tangible product comprises a tangible pharmaceutical product.

24. The method of claim 14, wherein the product dispensing system is a tablet dispensing system and the tangible product comprises a tablet.

25. A system, comprising:
   a processor; and
   a memory coupled to the processor and comprising computer readable program code embodied in the memory that when executed by the processor causes the processor to perform operations comprising:
   sniffing traffic on a communication network to copy packets comprising a print job that contains product labeling information corresponding to a tangible product without facilitating communication of the packets comprising the print job to a destination identified in the packets;
   filtering the packets, so as to remove fields from the packets that have been sniffed to generate filtered packets, the filtered packets comprising fields not removed from the packets that have been sniffed;
   combining the filtered packets to generate contiguous data;
   generating a command script based on the contiguous data;
   sending the command script to a product dispensing system over the communication network; and
   dispensing the tangible product using the product dispensing system responsive to receipt of the command script at the product dispensing system.

26. A system, comprising:
   a processor; and
   a memory coupled to the processor and comprising computer readable program code embodied in the memory that when executed by the processor causes the processor to perform operations comprising:
   sniffing traffic on a communication network to obtain copy packets comprising a print job that contains product labeling information corresponding to a tangible product without facilitating communication of the packets comprising the print job to a destination identified in the packets;

extracting information. corresponding to the tangible product from the packets comprising the print job;

organizing the information corresponding to the tangible product that was extracted into discrete informational units;

generating a command script based on the organized discrete informational units;

sending the command script to a product dispensing system over the communication network; and dispensing the tangible product using the product dispensing system responsive to receipt of the command script at the product dispensing system.

27. A computer program product, comprising:

a non-transitory computer readable storage medium comprising computer readable program code embodied in the medium that when executed by a processor causes the processor to perform operations comprising:

sniffing traffic on a communication network to copy packets comprising a print job that contains product labeling information corresponding to a tangible product without facilitating communication of the packets comprising the print job to a destination identified in the packets;

filtering the packets so as to remove fields from the packets that have been sniffed to generate filtered packets, the filtered packets comprising fields not removed from the packets that have been sniffed;

combining the filtered packets to generate contiguous data;

generating a command script based on the contiguous data;

sending the command script to a product dispensing system over the communication network; and dispensing the tangible product using the product dispensing system responsive to receipt of the command script at the product dispensing system.

28. A computer program product, comprising:

a non-transitory computer readable storage medium comprising computer readable program code embodied in the medium that when executed by a processor causes the processor to perform operations comprising:

sniffing traffic on a communication network to copy packets comprising a print job that contains product labeling information corresponding to a tangible product without facilitating communication of the packets comprising the print job to a destination identified in the packets;

extracting information corresponding to the tangible product from the packets comprising the print job;

organizing the information corresponding to the tangible product that was extracted into discrete informational units;

generating a command script based on the organized discrete informational units;

sending the command script to a product dispensing system over the communication network; and dispensing the tangible product using the product dispensing system responsive to receipt of the command script at the product, dispensing system.

* * * * *

UNITED STATES PATENT AND TRADEMARK OFFICE
CERTIFICATE OF CORRECTION

| | |
|---|---|
| PATENT NO. | : 11,128,601 B2 |
| APPLICATION NO. | : 12/199602 |
| DATED | : September 21, 2021 |
| INVENTOR(S) | : Cunningham et al. |

It is certified that error appears in the above-identified patent and that said Letters Patent is hereby corrected as shown below:

In the Claims

Column 12, Line 36, Claim 1: Please correct "the p tnt job" to read -- the print job --

Column 12, Line 50, Claim 1: Please correct "at, the product" to read -- at the product --

Column 13, Line 42, Claim 14: Please correct "infbrmation" to read -- information --

Column 14, Line 46, Claim 25: Please correct "packets, so as" to read -- packets so as --

Column 14, Lines 65-66, Claim 26: Please correct "to obtain copy" to read -- to copy --

Column 15, Line 4, Claim 26: Please correct "information. corresponding" to read -- information corresponding --

Column 15, Line 6, Claim 26: Please correct "infbrmation" to read -- information --

Column 16, Line 31, Claim 28: Please correct "product, dispensing system" to read -- product dispensing system --

Signed and Sealed this
Fifth Day of July, 2022

Katherine Kelly Vidal
*Director of the United States Patent and Trademark Office*